US00PP34478P2

(12) United States Plant Patent
von Tubeuf

(10) Patent No.: US PP34,478 P2
(45) Date of Patent: Aug. 2, 2022

(54) ***LOBELIA* PLANT NAMED 'KLELE20100'**

(50) Latin Name: *Lobelia erinus*
Varietal Denomination: 'KLELE20100'

(71) Applicant: Klemm+Sohn GmbH & Co. KG, Stuttgart (DE)

(72) Inventor: Guido von Tubeuf, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 17/373,323

(22) Filed: Jul. 12, 2021

(51) Int. Cl.
*A01H 5/02* (2018.01)
*A01H 6/26* (2018.01)

(52) U.S. Cl.
USPC ..... Plt./451
CPC ..... *A01H 6/268* (2018.05)

(58) Field of Classification Search
USPC ..... Plt./451
CPC ..... A01H 6/268
See application file for complete search history.

(56) References Cited

PUBLICATIONS

UPOV hit on *Lobelia* plant named, 'KLELE20100', QZ PBR 20211320, filed Jun. 10, 2021.*
CPVO documentation on the application of QZ PBR 20211320, filed Jun. 10, 2021 to a *Lobelia* plant named, 'KLELE20100'.*

* cited by examiner

*Primary Examiner* — Anne Marie Grunberg
(74) *Attorney, Agent, or Firm* — Weatherly IP Solutions, LLC; Barbara Campbell

(57) ABSTRACT

A new *Lobelia* plant particularly distinguished by a semi-upright and freely branching growth habit, medium vigor, and violet-blue flowers with white centers, is disclosed.

1 Drawing Sheet

Genus and species: *Lobelia erinus.*
Variety denomination: 'KLELE20100'.

BACKGROUND OF THE NEW PLANT

The present invention comprises a new and distinct variety of *Lobelia*, botanically known as *Lobelia erinus*, and hereinafter referred to by the variety name 'KLELE20100'. 'KLELE20100' originated from a controlled cross-pollination in Summer 2015 in Stuttgart, Germany between the proprietary female *Lobelia* variety 'LE-2015-5141' (unpatented) and the proprietary male *Lobelia* variety 'LE-2012-0015' (unpatented).

The seeds from the cross were sown and plants were grown in a greenhouse for evaluation, where an individual plant designated 'KLELE20100' was selected from the group. 'KLELE20100' was first vegetatively propagated via apical vegetative cuttings. 'KLELE20100' was found to reproduce true to type in successive generations of asexual propagation via apical vegetative cuttings.

SUMMARY

The following are the most outstanding and distinguishing characteristics of this new variety when grown under normal horticultural practices in Stuttgart, Germany.

1. A semi-upright and freely branching growth habit;
2. Medium vigor; and
3. Violet-blue flowers with white centers.

DESCRIPTION OF THE PHOTOGRAPH

This new *Lobelia* plant is illustrated by the accompanying photograph which shows the plant's overall plant habit including form, foliage, and flowers. The photograph is of a 4-month-old plant grown in a glass greenhouse in Stuttgart, Germany in March 2021. The colors shown are as true as can be reasonably obtained by conventional photographic procedures.

DESCRIPTION OF THE NEW VARIETY

The following detailed descriptions set forth the distinctive characteristics of 'KLELE20100'. The data which define these characteristics were collected from asexual reproductions carried out in Stuttgart, Germany. Data was collected on 8-week-old plants grown in a greenhouse in Stuttgart, Germany in May 2021. Color references are to The R.H.S. Colour Chart of The Royal Horticultural Society of London (R.H.S.), 5$^{th}$ edition (2007).

Classification:
- *Family.*—Campanulaceae.
- *Botanical.—Lobelia erinus.*
- *Common.—Lobelia.*
- *Designation.*—'KLELE20100'.

Parentage:
- *Female parent.*—The proprietary female *Lobelia* variety 'LE-2015-5141' (unpatented).
- *Male parent.*—The proprietary male *Lobelia* variety 'LE-2012-0015' (unpatented).

Growth:
- *Growth and branching habit.*—Semi-upright, freely branching.
- *Form.*—Triangular.
- *Height (measured from the top of the soil including any flowers).*—17.0 cm.

*Width* (*horizontal plant diameter, including any flowers*).—26.0 cm.
*Time to produce a finished flowering plant.*—8 weeks.
*Outdoor plant performance*.—Good.
*Time to initiate roots.*—2 to 3 weeks.
*Root description*.—Fine, white roots, freely branching, and dense.

Leaves:
*Arrangement*.—Alternate.
*Color*.—Immature Leaf: Upper surface: RHS 137A (Green). Lower surface: RHS N138B (Green). Mature Leaf: Upper surface: RHS 137A (Green). Lower surface: RHS N138B (Green).
*Length*.—5.0 cm to 6.0 cm.
*Width*.—About 1.5 cm.
*Shape*.—Elliptical.
*Margin*.—Serrate.
*Apex*.—Obtuse.
*Base*.—Attenuate.
*Texture* (*both surfaces*).—Smooth.
*Venation*.—Pinnate.
*Venation color*.—Upper surface: Transparent, R.H.S. color not available. Lower surface: RHS 137B (Green).

Stems:
*Length*.—15.0 cm.
*Diameter*.—0.2 cm.
*Internode length*.—1.0 cm to 2.0 cm.
*Color*.—RHS N137C (Green).
*Texture*.—Smooth.
*Stem anthocyanin*.—Absent.
*Peduncle*.—Length: 1.0 cm to 3.0 cm. Diameter: 0.05 cm. Texture: Smooth. Color: RHS N137C (Green).

Flower buds:
*Shape*.—Inverse drop-shaped.
*Diameter*.—0.25 cm to 0.3 cm.
*Length*.—0.8 cm to 1.0 cm.
*Color*.—RHS 138D (Green).

Inflorescence:
*Blooming habit*.—Continuous.
*Lastingness of individual blooms on plant*.—Approximately 1 week.
*Fragrance*.—Absent.
*Inflorescence type*.—Raceme.
*Quantity of flowers and buds per flowering branch*.—8 to 10.

Flowers:
*Flower diameter* (*horizontal*).—About 2.0 cm.
*Flower height* (*vertical*).—0.5 cm to 0.6 cm.
*Mature flower*.—Upper lobe: Color, upper surface: Between RHS 95A (Violet-Blue) and RHS 95B (Violet-Blue). Length: 0.7 cm. Width: 0.3 cm. Shape: Spatulate. Apex: Mucronate. Margin: Entire. Texture (both upper and lower surfaces): Smooth, but upper surface also has very short hairs along the margins. Lower lobe: Color, upper surface: Between RHS 95A (Violet-Blue) and RHS 95B (Violet-Blue). Color, lower surface: RHS 94A (Violet-Blue). Length: 1.2 cm. Width: 0.8 cm. Shape: Orbicular. Apex: Mucronate. Margin: Entire. Texture (both upper and lower surfaces): Smooth.
*Corolla tube*.—Color inside: RHS N155D (White). Color outside: RHS N155D (White) with RHS 94A (Violet-Blue) stripes. Tube length: 0.7 cm. Diameter: 0.5 cm.
*Calyx*.—Length: 1.0 cm (can include an additional 0.4 cm for the fused part). Diameter: 0.2 cm (measured at the fusion point). Shape: Composed of 5 narrowly triangular single leaflets forming a star shaped calyx fused in the lower quarter. Apex: Narrowly acute. Texture: Smooth. Color: RHS 137A (Green).

Reproductive organs:
*Stamens*.—Quantity per flower: 5. Filament length: 0.7 cm. Filament color: RHS 97B (Violet-Blue). Anther length: 0.8 cm. Anther width: 0.1 cm. Anther color: Close to RHS 94A (Violet-Blue). Pollen color: RHS 3D (Yellow). Pollen amount: Sparse.
*Pistils*.—Stigma color: RHS N89B (Violet-Blue) for immature and mature color not observed. Style length: 0.8 cm. Style color: RHS 147C (Yellow-Green). Ovary color: RHS 145C (Yellow-Green). Ovary shape: Ovate.

Fruit and seed set: Fruit and seed set not observed.
Disease and pest/insect resistance: No disease and pest/insect resistance observed.

COMPARISON WITH PARENTAL LINES AND KNOWN VARIETY

'KLELE20100' can be distinguished from its parents as described in Table 1.

TABLE 1

Comparison with Parental Lines

| Characteristic | 'KLELE20100' | Female Parent 'LE-2015-5141' | Male Parent 'LE-2012-0015' |
|---|---|---|---|
| Habit | Semi-upright | | Horizontal |
| Vigor | Medium | Compact | Compact |

'KLELE20100' is most similar to the commercial *Lobelia* variety 'KLELE13407' (unpatented) and also known as 'Compact Dark Blue'. Differences between the varieties are described in Table 2.

TABLE 2

Comparison with Similar Variety

| Characteristic | 'KLELE20100' | 'KLELE13407' |
|---|---|---|
| Vigor | Medium | Low |
| Earliness to flower | Earlier than 'KLELE13407' | Approximately 1 week later than 'KLELE20100' |

I claim:

1. A new and distinct variety of *Lobelia* plant designated 'KLELE20100' as illustrated and described herein.

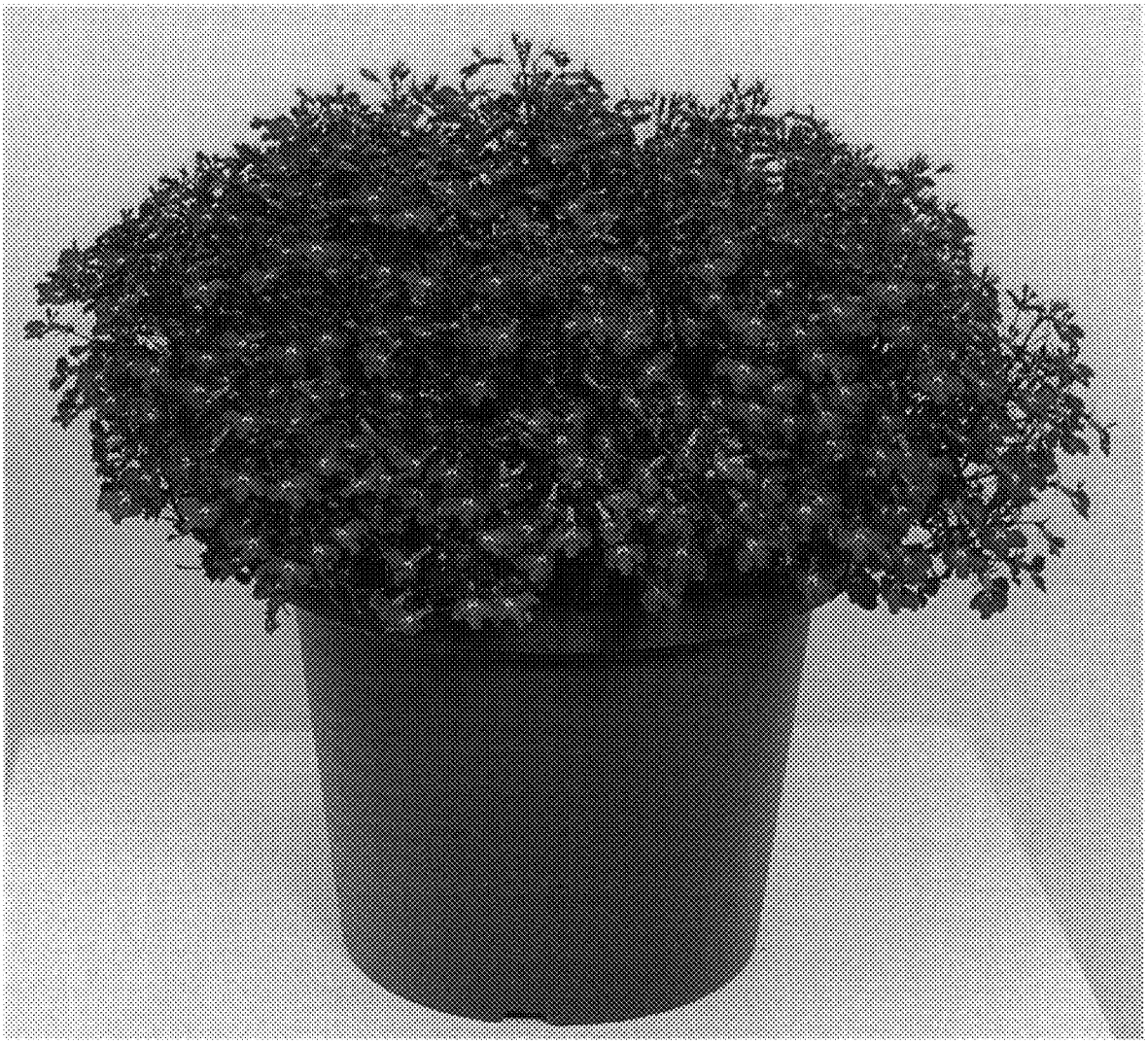

* * * * *